(12) United States Patent  
Robich

(10) Patent No.: US 11,696,784 B2  
(45) Date of Patent: Jul. 11, 2023

(54) ANGLED SURGICAL TROCARS

(71) Applicant: Maine Medical Center, Portland, ME (US)

(72) Inventor: Michael P. Robich, Yarmouth, ME (US)

(73) Assignee: Maine Medical Center, Portland, ME (US)

(*) Notice: Subject to any disclaimer, the term of this patent is extended or adjusted under 35 U.S.C. 154(b) by 435 days.

(21) Appl. No.: 16/256,098

(22) Filed: Jan. 24, 2019

(65) Prior Publication Data

US 2019/0231388 A1    Aug. 1, 2019

Related U.S. Application Data

(60) Provisional application No. 62/622,264, filed on Jan. 26, 2018.

(51) Int. Cl.
*A61B 17/34* (2006.01)
*A61B 17/02* (2006.01)
*A61M 25/00* (2006.01)

(52) U.S. Cl.
CPC ...... *A61B 17/3423* (2013.01); *A61B 17/3417* (2013.01); *A61B 17/3421* (2013.01);
(Continued)

(58) Field of Classification Search
CPC ............ A61B 2017/0225; A61B 17/34; A61B 17/3415; A61B 17/3417; A61B 17/3421; A61B 17/3423; A61B 17/3431; A61B 2017/3454; A61B 2017/3456; A61B 17/3496
(Continued)

(56) References Cited

U.S. PATENT DOCUMENTS 5,509,909 A    4/1996 Moy
5,554,138 A    9/1996 Stanford et al.
(Continued)

FOREIGN PATENT DOCUMENTS

EP    577400 A1    1/1994
EP    1970012 B1    11/2011
(Continued)

OTHER PUBLICATIONS

International Search Report and Written Opinion for International App. No. PCT/US19/14881 dated Apr. 24, 2019 (13 pages).

*Primary Examiner* — Si Ming Ku
(74) *Attorney, Agent, or Firm* — McCarter & English, LLP; David G. Conlin; Alexa Marie J. Derkasch

(57) ABSTRACT

Various exemplary angled surgical trocars and methods of using angled surgical trocars are provided. In general, a trocar configured to be advanced into a body of a patient can have an angled distal portion. The trocar can have a cut-out at its distal end in the angled distal portion of the trocar. The trocar can be advanced into the patient's body alone or with an obturator located therein. The obturator located in the trocar can have a flexible portion configured to bend within the trocar's angled distal portion. The trocar and obturator can be used in a variety of medical procedures, for example thoracic procedures in which the trocar is used to provide access to a thoracic cavity of a patient.

20 Claims, 5 Drawing Sheets

(52) U.S. Cl.
CPC .. *A61B 17/3496* (2013.01); *A61B 2017/0225* (2013.01); *A61B 2017/3454* (2013.01); *A61M 25/0041* (2013.01)

(58) Field of Classification Search
USPC .................................................. 600/204, 205
See application file for complete search history.

(56) References Cited

U.S. PATENT DOCUMENTS

| | | |
|---|---|---|
| 5,562,677 A | 10/1996 | Hildwein et al. |
| 5,817,062 A | 10/1998 | Flom et al. |
| 5,971,960 A | 10/1999 | Flom et al. |
| 7,326,197 B2 | 2/2008 | Breznock et al. |
| 8,795,150 B2 | 8/2014 | Forsell |
| 2006/0025797 A1* | 2/2006 | Lock ................. A61B 17/3401 606/191 |
| 2006/0206097 A1 | 9/2006 | Breznock et al. |
| 2009/0209913 A1 | 8/2009 | Ferrari |
| 2010/0280368 A1* | 11/2010 | Can .......................... A61B 1/31 604/167.03 |
| 2012/0232552 A1* | 9/2012 | Morgenstern Lopez ................... A61B 5/24 606/45 |
| 2013/0131549 A1 | 5/2013 | Kristensen et al. |
| 2014/0142366 A1 | 5/2014 | Forsell |
| 2016/0310194 A1* | 10/2016 | Elser .................. A61B 17/8811 |
| 2017/0238962 A1* | 8/2017 | Hansen .............. A61B 17/3421 |
| 2019/0091459 A1* | 3/2019 | Donaldson ......... A61B 17/3498 |

FOREIGN PATENT DOCUMENTS

| | | |
|---|---|---|
| GB | 1149849 A | 4/1969 |
| WO | WO-1997033520 A1 | 9/1997 |
| WO | WO-2004016184 A1 | 2/2004 |
| WO | WO-2010042016 A1 | 4/2010 |

* cited by examiner

ANGLED SURGICAL TROCARS

CROSS REFERENCE TO RELATED APPLICATIONS

The present application claims priority to U.S. Provisional Patent Application No. 62/622,264 entitled "Angled Surgical Trocars" filed Jan. 26, 2018, which is hereby incorporated by reference in its entirety.

FIELD

The present disclosure relates generally to angled surgical trocars.

BACKGROUND

Access to an organ or body space of a patient may be needed in the course of medical diagnosis or treatment for a variety of different reasons. For example, a pericardial space of a patient's heart may need to be accessed as part of performing a heart treatment. Trocars are a type of surgical access device that can be used to access the organ or body space. However, it can be difficult for even experienced medical professionals to access organs and body spaces quickly and accurately without causing patient discomfort, without causing inadequate drainage, and/or without first experiencing one or more failed attempts in inserting the trocar into the patient. These risks are increased in obese patients and muscular patients. Image guidance, e.g., ultrasound, has been used to assist medical professionals in accessing organs and body spaces, but imaging equipment is not always available, can be impractical to use in trauma situations, can be costly, can require training to use, and does not always provide consistent results.

Accordingly, there remains a need for improved surgical trocars.

SUMMARY

In general, angled surgical trocars and methods of using angled surgical trocars are provided.

In one aspect, a surgical device is provided that in one embodiment includes a trocar configured to be positioned in tissue of a patient to allow access therethrough into a body cavity of the patient. The trocar includes a tubular elongate body having a proximal portion defining a first longitudinal axis. The tubular elongate body has a distal portion defining a second longitudinal axis that is transverse to the first longitudinal axis such that the distal portion extends at an angle with respect to the proximal portion. The tubular elongate body has an inner lumen extending through the proximal and distal portions, and the inner lumen is configured to slidably receive a surgical tool therein to allow passage of the surgical tool therethrough from outside the patient to inside the body cavity.

The surgical device can have any number of variations. For example, the tubular elongate body can have a cut-out in a sidewall thereof at a distal-most end of the tubular elongate body. In at least some embodiments, the cut-out can have a longitudinal length that is less than a longitudinal length of the distal portion.

For another example, a longitudinal length of the distal portion can be less than a longitudinal length of the proximal portion. In at least some embodiments, the longitudinal length of the distal portion can be about ⅓ of the longitudinal length of the proximal portion.

For yet another example, the angle can be fixed.

For still another example, the angle can be in a range of about 120° to 170°. In at least some embodiments, the angle can be about 155°.

For another example, the tubular elongate body can be rigid.

For yet another example, the trocar can have a proximal housing from which the tubular elongate body distally extends, and a distal surface of the proximal housing can be configured to abut an exterior surface of the tissue through which the tubular elongate body extends.

In another embodiment, a surgical device includes an obturator having a rigid distal tip configured to penetrate through tissue of a patient to lead the obturator into a body cavity of the patient. The obturator is configured to be inserted into an inner lumen of a trocar and advanced distally therethrough such that the rigid distal tip of the obturator is located distally beyond the trocar. The obturator has an elongate shaft with a rigid proximal portion and a flexible intermediate portion located between the rigid proximal portion and the rigid distal tip. The flexible intermediate portion is configured to bend within the trocar such that the obturator is positioned relative to the trocar with the rigid proximal portion located within the inner lumen, the flexible intermediate portion bent within the inner lumen, and the rigid distal tip located distally beyond the trocar.

The surgical device can vary in any number of ways. For example, the flexible intermediate portion can have a first state, in which a longitudinal axis thereof is coaxially aligned with a longitudinal axis of the rigid proximal portion and a longitudinal axis of the rigid distal tip, and a second state, in which the longitudinal axis of the flexible intermediate portion is coaxially aligned with the longitudinal axis of the rigid distal tip and is transverse to the longitudinal axis of the rigid proximal portion such that a distal portion of the obturator including the flexible intermediate portion and the distal tip extends at an angle with respect to the rigid proximal portion. In at least some embodiments, the flexible intermediate portion can be configured to dynamically move between the first and second states in response to sliding within the inner lumen of the trocar.

For another example, the distal tip can have a blunt end.

For yet another example, the obturator can be configured to be removed from the inner lumen by being slid proximally therethrough.

For still another example, the obturator can have a proximal handle portion from which the elongate shaft distally extends.

In another aspect, a surgical system is provided that in one embodiment includes a trocar and an obturator. The trocar is configured to be positioned in tissue of a patient to allow access therethrough into a body cavity of the patient. The trocar includes a tubular elongate body having a proximal portion defining a first longitudinal axis. The tubular elongate body has a distal portion defining a second longitudinal axis that is transverse to the first longitudinal axis such that the distal portion extends at an angle with respect to the proximal portion. The tubular elongate body has an inner lumen extending through the proximal and distal portions. The obturator is configured to be inserted into the inner lumen and advanced distally therethrough such that a rigid distal tip of the obturator is located distally beyond the tubular body. The obturator has an elongate shaft with a rigid proximal portion and a flexible intermediate portion located between the rigid proximal portion and the rigid distal tip. The flexible intermediate portion is configured to bend within the distal portion of the tubular elongate body.

The surgical system can have any number of variations. For example, the flexible intermediate portion can have a first state, in which a longitudinal axis thereof is coaxially aligned with a longitudinal axis of the rigid proximal portion and a longitudinal axis of the rigid distal tip, and a second state, in which the longitudinal axis of the flexible intermediate portion is coaxially aligned with the longitudinal axis of the rigid distal tip and is transverse to the longitudinal axis of the rigid proximal portion such that a distal portion of the obturator including the flexible intermediate portion and the distal tip extends at a second angle with respect to the rigid proximal portion. In at least some embodiments, the flexible intermediate portion can be configured to automatically move between the first and second states in response to sliding within the inner lumen, and/or the angle and the second angle can be substantially equal.

For another example, the obturator can have a blunt end configured to penetrate through the tissue of the patient to lead the trocar and obturator into the body cavity.

For yet another example, the obturator can be configured to be removed from the inner lumen by being slid proximally therethrough.

For another example, the obturator can have a proximal handle portion from which the elongate shaft distally extends.

For still another example, the tubular elongate body can have a cut-out in a sidewall thereof at a distal-most end of the tubular elongate body. In at least some embodiments, the cut-out can have a longitudinal length that is less than a longitudinal length of the distal portion of the tubular elongate body.

For yet another example, a longitudinal length of the distal portion of the tubular elongate body can be less than a longitudinal length of the proximal portion of the tubular elongate body. In at least some embodiments, the longitudinal length of the distal portion of the tubular elongate body can be about ⅓ of the longitudinal length of the proximal portion of the tubular elongate body.

For another example, the angle can be fixed.

For yet another example, the angle can be in a range of about 120° to 170°. In at least some embodiments, the angle can be about 155°.

For still another example, the tubular elongate body can be rigid.

For yet another example, the trocar can have a proximal housing from which the tubular elongate body distally extends, and a distal surface of the proximal housing can be configured to abut an exterior surface of the tissue through which the tubular elongate body extends.

In another aspect, a surgical method is provided that in one embodiment includes advancing a trocar and an obturator as a unit through tissue of a patient at an angle relative to a surface of the tissue until distal ends of each of the trocar and obturator enter a body cavity underlying the tissue, and then changing the angle of the trocar and obturator relative to the surface of the tissue. The obturator is located within an inner lumen of the trocar with a distal tip of the obturator located distal to the trocar and leading the unit through the tissue. The angle at which the trocar and obturator are advanced through the tissue is defined by a curved distal portion of the trocar that is curved at a fixed angle relative to a proximal portion of the trocar. The angle is changed such that a longitudinal axis of the proximal portion of the trocar is substantially perpendicular to the surface of the tissue.

The surgical method can have any number of variations. For example, the trocar can have a cut-out in a sidewall thereof at a distal-most end of the trocar, and the cut-out can face upward during the advancement of the trocar and obturator through the tissue.

For another example, the angle can be in a range of about 120° to 170°. In at least some embodiments, the angle can be about 155°.

For yet another example, the body cavity can be a thoracic cavity.

For still another example, the distal tip of the obturator can have a blunt end.

For yet another example, the surgical method can include, before advancing the trocar and obturator as the unit through the tissue of a patient, inserting the obturator into the trocar and advancing the obturator distally within the trocar until the distal tip is located distal to the trocar. In at least some embodiments, the distal tip of the obturator can be rigid, the obturator can have an elongate shaft with a rigid proximal portion and a flexible intermediate portion located between the rigid proximal portion and the rigid distal tip, and the flexible intermediate portion can automatically bend at the curved distal portion within the trocar during the distal advancement of the obturator within the trocar.

For another example, the surgical method can include, after changing the angle, removing the obturator from the trocar to allow a surgical tool to be advanced through the trocar and into the body cavity from outside the patient. In at least some embodiments, the surgical tool can be a chest tube.

BRIEF DESCRIPTION OF DRAWINGS

This invention will be more fully understood from the following detailed description taken in conjunction with the accompanying drawings, in which.

DETAILED DESCRIPTION

Figure 1:
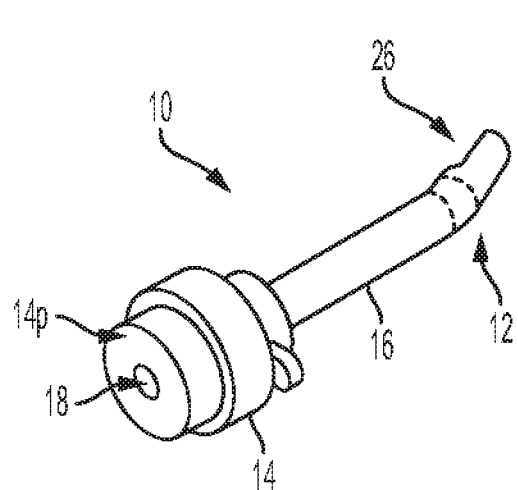
FIG. 1 is a perspective view of one embodiment of a trocar.
Figure 2:
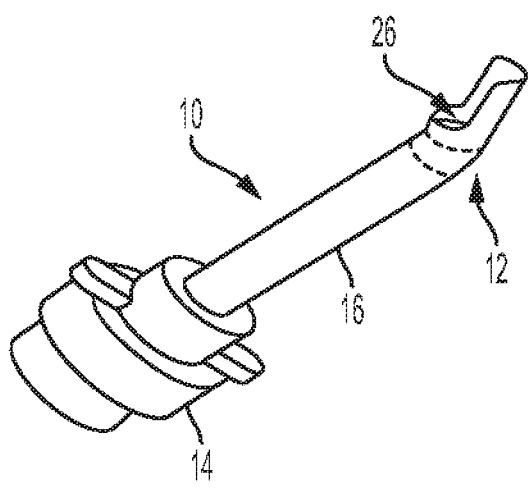
FIG. 2 is another perspective view of the trocar of FIG. 1.
Figure 3:
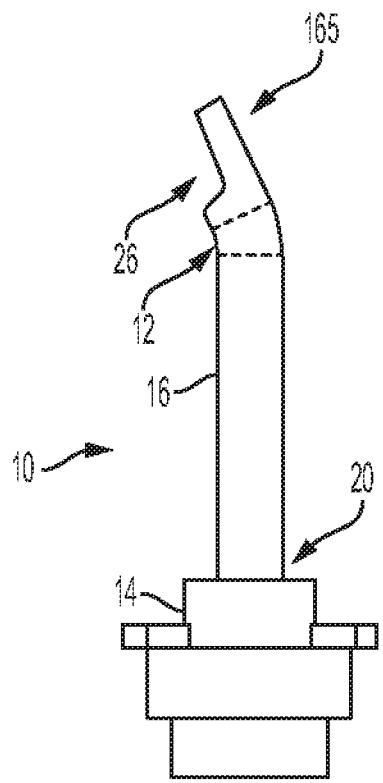
FIG. 3 is a side view of the trocar of FIG. 1.
Figure 4:
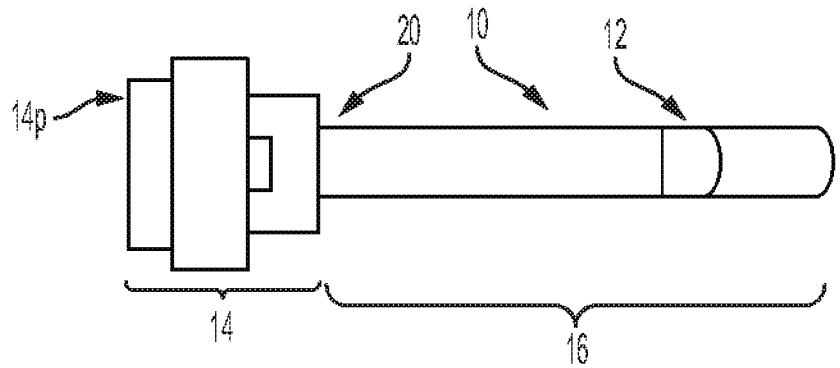
FIG. 4 is side view of the trocar of FIG. 1 from a different side than in FIG. 3.
Figure 5:
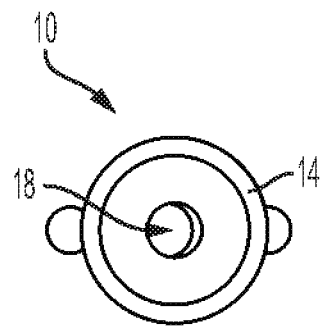
FIG. 5 is a top view of the trocar of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary angled surgical trocars and methods of using angled surgical trocars are provided. In general, a trocar configured to be advanced into a body of a patient can have an angled distal portion. The angled portion may allow the trocar to be more safely and more predictably positioned within a patient than a traditional trocar that is straight (non-angled). The angle of the distal portion can be fixed, which may help steer the trocar through tissue to allow secure, predictable advancement of the trocar through tissue. The trocar can have a cut-out at its distal end in the angled distal portion of the trocar. The cut-out can be configured to reduce an amount of friction between the trocar and tissue through which the trocar is being advanced distally, which may speed entry of the trocar into the patient and/or reduce tissue trauma experienced by the patient from trocar insertion.

The trocars described herein can be advanced into the patient's body alone or with an obturator located therein. The obturator located in the trocar can have a flexible portion configured to bend within the trocar's angled distal portion. The obturator's distal tip located distal to the flexible portion can be rigid, which may facilitate penetration of the obturator into tissue as the distal tip leads the trocar/obturator unit through the tissue until distal ends of the trocar and obturator enter a body cavity underlying the tissue. Obturator use can be particularly useful in helping to advance the trocar through thicker tissue, e.g., tissue having a thickness in a range of about 2 to 4 inches. Obturators traditionally have straight, rigid shafts, so traditional obturators cannot be used with the trocar having an angled distal portion since the obturator could not bend at the angled distal portion.

The trocars and obturators described herein can be used in a variety of medical procedures. In an exemplary embodiment, the trocars and obturators can be used in thoracic procedures in which the trocar is used to provide access to a thoracic cavity of a patient. Thoracic cavity access is often needed in trauma situations in which action must be taken quickly. The trocars and obturators described herein providing safe, predictable, and fast access to the thoracic cavity (or other body cavity) may thus speed treatment of the patient in trauma situations in which speedy treatment is particularly critical and when imaging to facilitate trocar placement is impractical for time reasons. For example, chest tubes are commonly used in trauma situations, emergency room care, thoracic surgery, and pulmonology, and a trocar providing access to a thoracic cavity may allow a chest tube to be advanced into the thoracic cavity through the trocar in a safe, predictable, and fast manner with the chest tube more reliably inserted into the thoracic cavity at an appropriate position and angle.

Figure 6:
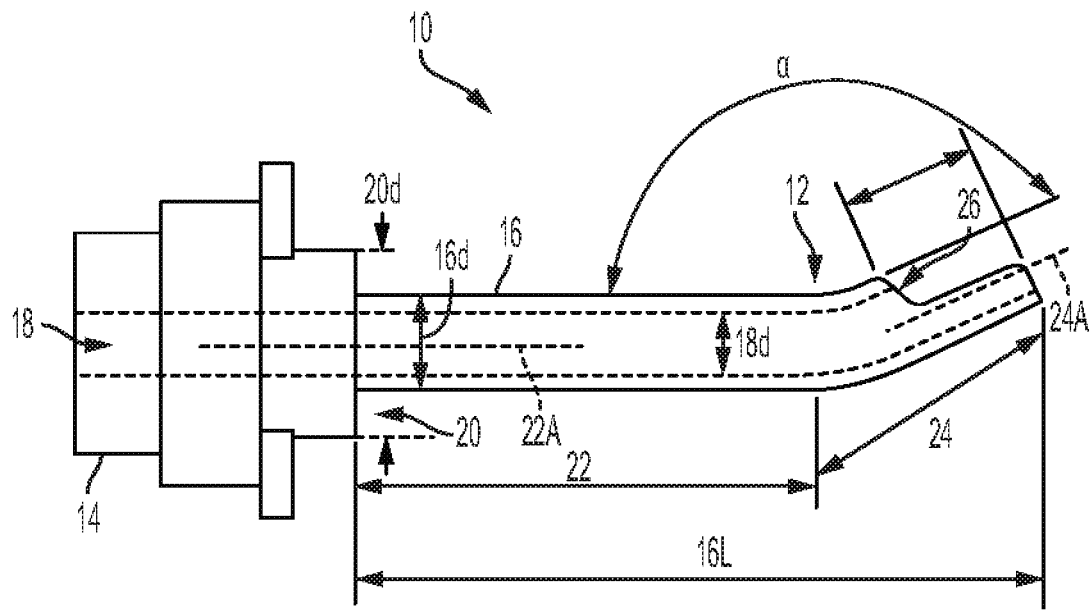
FIG. 6 is a side, partially transparent view of the trocar of FIG. 1.
Figure 7:
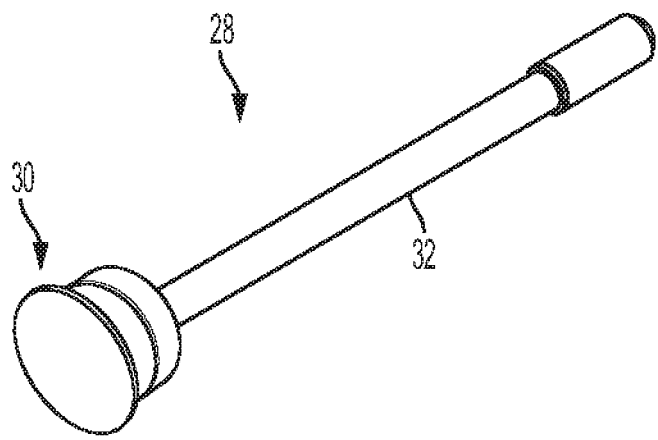
FIG. 7 is a perspective view of one embodiment of an obturator.
Figure 8:
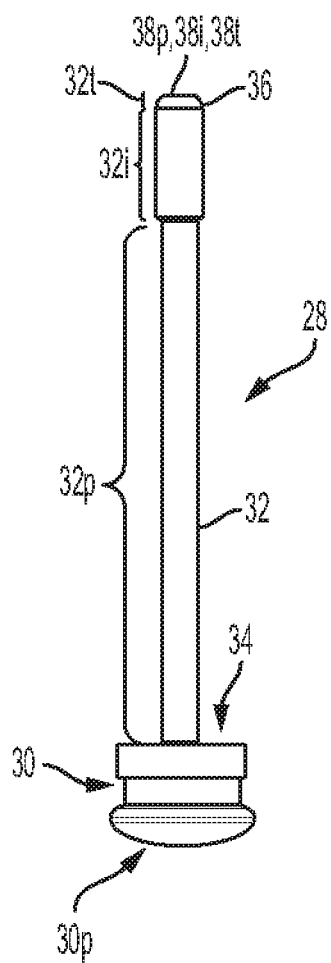
FIG. 8 is a side view of the obturator of FIG. 7.

FIGS. 1-6 illustrate one embodiment of a trocar 10 having a curved portion 12 in a distal portion of the trocar 10. The trocar 10 includes a housing 14 at a proximal end thereof and includes an elongate tubular body 16 extending distally from the housing 14. The elongate tubular body 16 includes the curved portion 12. The trocar 10 has an inner lumen 18 extending therethrough that, as shown in FIG. 6, includes a proximal portion in the housing 14 and a distal portion in the elongate tubular body 16. The trocar 10 is thus cannulated.

The housing 14 can have a variety of configurations, as will be appreciated by a person skilled in the art. Regardless of the housing's particular configuration, in an exemplary embodiment, as in this illustrated embodiment, the housing 14 has a distal surface 20 configured to abut an exterior surface of tissue (e.g., an exterior skin surface) in which the trocar 10 is positioned, e.g., through the which elongate tubular body 16 extends to provide access to a body cavity underlying the tissue. The abutment of the housing's distal surface 20 against the tissue surface may help maintain a position of the trocar 10 relative to the tissue and may help prevent the trocar 10 from moving entirely into the patient. As shown in FIG. 6, the distal surface 20 has a diameter 20d that is greater than an outer diameter 16d of the elongate tubular body 16 to help prevent the trocar 10 from moving entirely into the patient. Since an opening in tissue in which the elongate tubular body 16 is positioned is typically made as small as possible to facilitate cosmesis, to reduce tissue trauma, to reduce bleeding, etc., the housing's distal surface 20 having a diameter 20d greater than the elongate tubular body's outer diameter 16d will prevent the housing 14 from entering into the opening formed in the tissue and hence keep the trocar 10 partially outside of the patient's body. The diameter 20d of the housing's distal surface 20 is thus also greater than a diameter 18d of the trocar's inner lumen 18, which is less than the outer diameter 16d of the elongate tubular body 16. The inner lumen's diameter 18d is about 10 mm (about 0.39 in) in this illustrated embodiment, but the inner lumen's diameter 18d can have other sizes. A person skilled in the art will appreciate that a value may not be precisely at a particular value but nevertheless be considered to be about that value for any of a variety of reasons, such as manufacturing tolerances and sensitivity of measurement equipment.

The elongate tubular body 16 has a proximal portion 22 and has a distal portion 24 that is angled relative to the proximal portion 22 due to the curved portion 12 of the trocar 10. The proximal portion 22 defines a first longitudinal axis 22A, and the distal portion 24 defines a second longitudinal axis 24A. As shown in FIG. 6, the second longitudinal axis 24A is at an angle α relative to the first longitudinal axis 22A. The angle α can be in a range of about 120° to 170°. In an exemplary embodiment, the angle α is about 155°. The first longitudinal axis 22A of the elongate tubular body's proximal portion 22 is coaxially aligned with a longitudinal axis 14A of the proximal housing 14, as also shown in FIG. 6.

At least the elongate tubular body 16 of the trocar 10 is rigid. The angle α is therefore fixed. In other words, the curvature of the distal portion 24 is fixed relative to the proximal portion 22, e.g., the second longitudinal axis 24A is at a fixed angle α relative to the first longitudinal axis 22A.

The trocar 10 may thus be configured to predictably steer through tissue and to guide a surgical tool through the trocar 10 to facilitate proper positions of the surgical tool within a patient.

The elongate tubular body's proximal and distal portions 22, 24 can have various longitudinal lengths to allow different trocars to have different sizes appropriate for use with differently sized patients and for access to different body cavities. As in this illustrated embodiment, the distal portion 24 can have a longitudinal length that is about ⅓ of the longitudinal length of the proximal portion 22. The curved portion 12 can thus be located about ¾ of the way down (distally) of the elongate tubular body's longitudinal length, which may help ensure that the curved portion 12 is located entirely within a body cavity when the elongate tubular body 16 is positioned in tissue regardless of the tissue's thickness and that, accordingly, a chest tube or other surgical tool inserted into the trocar's inner lumen 18 is appropriately guided at a curve into the body cavity. AS one example, as in this illustrated embodiment, the longitudinal length of the proximal portion 22 can be about 71.7 mm (about 2.82 in), and a total longitudinal length 16L of the elongate tubular body 16 can be about 106.3 mm (about 4.19 in).

The trocar 10 includes a cut-out 26 in the elongate tubular body 16. The cut-out 26 is configured to reduce friction between the trocar 10 (e.g., the elongate tubular body 16 thereof) and tissue during the insertion of the trocar 10 through tissue. Reducing this friction may ease entry of the trocar 10 into the tissue and/or may reduce trauma to the tissue caused by the trocar's insertion. The cut-out 26 is in the sidewall of the elongate tubular body 16, as shown in FIGS. 1-3 and 6. The cut-out 26 is located entirely in the distal portion 24 of the elongate tubular body 16 and is at a distal-most end of the elongate tubular body 16. The cut-out 26 is on a side of the elongate tubular body 16 in a direction of the elongate tubular body's curvature. The side 16s of the elongate tubular body 16 opposite to the cut-out 26 (see FIG. 3) is thus configured to slide against tissue during passage of the trocar 10 through the tissue with the cut-out 26 preventing the entire circumference of the elongate tubular body 16 from sliding against the tissue since some of the sidewall is absent, thereby reducing friction between the elongate tubular body 16 and the tissue as compared to if the cut-out 26 was not present.

The cut-out 26 has a longitudinal length 26L that is less than the longitudinal length of the elongate tubular body's distal portion 24. The cut-out 26 can thus be located entirely distal to the curved portion 12 of the elongate tubular body 16, as shown in FIG. 6. As one example, as in this illustrated embodiment, the longitudinal length 26L of the cut-out 26 can be about 21.6 mm (about 0.85 in).

The trocar 10 can be made from any of a variety of one more materials. In an exemplary embodiment, the material(s) are surgically safe. Examples of materials that can be used for the trocar 10 include stainless steel and biocompatible plastics.

The trocar 10 can have a variety of additional features to facilitate its use, as will be appreciated by a person skilled in the art, such as any one or more of an instrument seal configured to seal the trocar's inner lumen 18 when a surgical tool is disposed therein, a channel seal configured to seal the trocar's inner lumen 18 when a surgical tool is not disposed therein, grip features on the trocar's proximal housing 14 to facilitate manual handling of the proximal housing 14, a marking to indicate a size of the trocar 10, etc.

FIGS. 7-10 illustrate one embodiment of an obturator 28 configured to be removably and replaceably disposed in a trocar having a curved portion, such as the trocar 10 of FIGS. 1-6. The obturator 28 includes a handle 30 at a proximal end thereof and includes an elongate shaft 32 extending distally from the handle 30.

Figure 9:
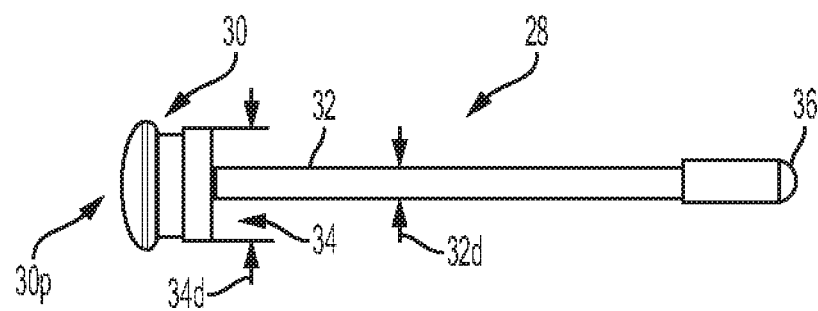
FIG. 9 is another side view of the obturator of FIG. 7 from a different side than in FIG. 8.
Figure 10:
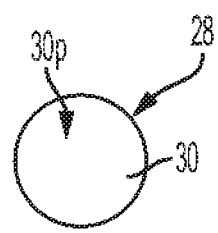
FIG. 10 is a top view of the obturator of FIG. 7.

The handle 30 can have a variety of configurations, as will be appreciated by a person skilled in the art. Regardless of the handle's particular configuration, in an exemplary embodiment, the handle 30 has a distal surface 34 configured to abut a proximal surface of a trocar in which the obturator 28 is slidably disposed, e.g., a proximal surface 14p of the housing 14 of the trocar 10 of FIGS. 1-6. The abutment of the handle's distal surface 34 against the trocar may help prevent the obturator's proximal end from moving into the trocar (e.g., into the trocar's inner lumen) where the obturator 28 can no longer be easily manipulated. As shown in FIG. 9, the handle's distal surface 34 has a diameter 34d that is greater than an outer diameter 32d of the elongate shaft 32, at least in a proximal portion 32p of the elongate shaft 32 configured to be disposed within the trocar's inner lumen, to facilitate the prevention of the obturator 28 from moving into the trocar. The diameter 34d of the handle's distal surface 34 is thus configured to be greater than a diameter of the trocar's inner lumen in which the obturator's elongate shaft 32 is configured to be disposed.

The obturator's handle 30 can be configured to be handled manually by a user (e.g., a surgeon, a surgeon's assistant, a pulmonologist, etc.) or by a robotic surgical system. As in this illustrated embodiment, the handle 30 can have a curved proximal surface 30p configured for a user's palm to comfortably rest and/or push thereagainst.

The obturator's elongate shaft 32 has a proximal portion 32p, a distal portion 32t (also referred to herein as a "distal tip portion" of the obturator 28), and an intermediate portion 32i that is located between the proximal portion 32p and the distal tip potion 32t. The proximal and distal portions 32p, 32t of the elongate shaft 32 are rigid, and the intermediate portion 32i of the elongate shaft 32 is flexible. The proximal portion 32p being rigid helps the elongate shaft 32 enter and smoothly slide within a trocar's inner lumen. The distal tip portion 32t being rigid helps the obturator 28 penetrate tissue at the obturator's distal tip 36. The distal tip 36 can have a blunt distal end, as in this illustrated embodiment, which may also help the obturator 28 penetrate tissue. The intermediate portion 32i being flexible allows the obturator 28 to bend within a curved portion of a trocar.

Figure 11:
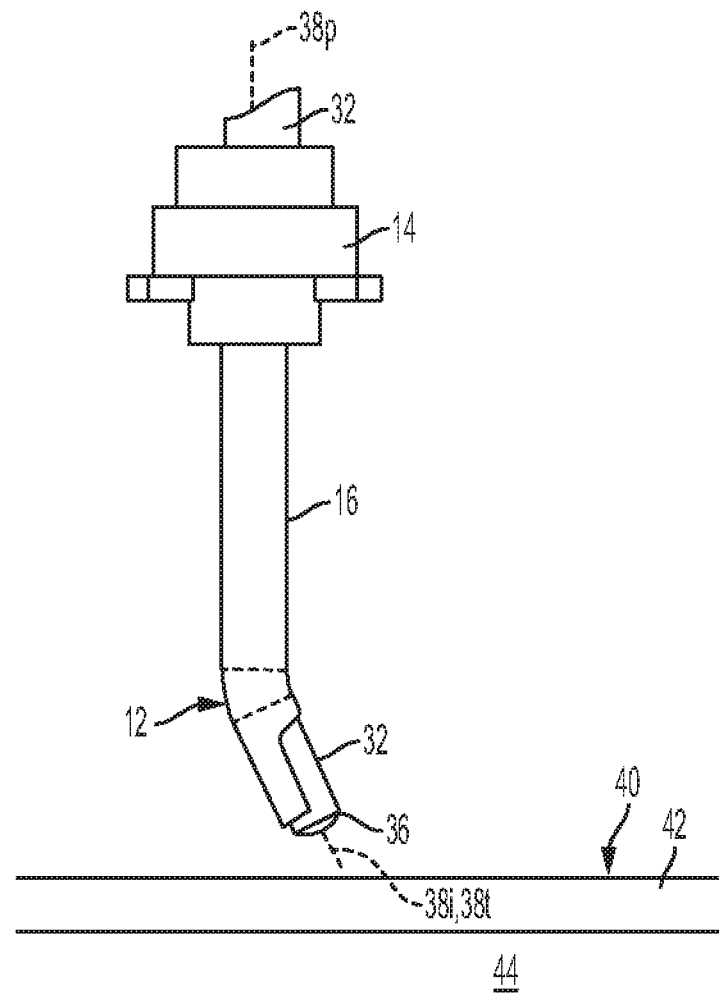
FIG. 11 is a side view of the obturator of FIG. 7 disposed in the trocar of FIG. 1 and positioned near tissue.
Figure 12:
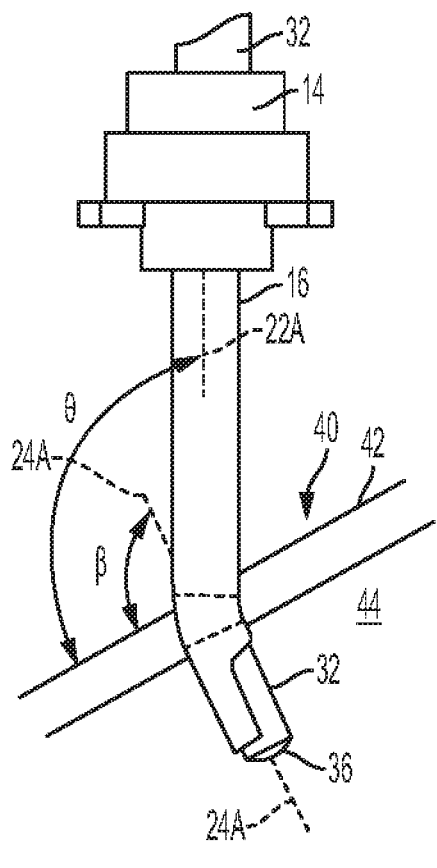
FIG. 12 is a side view of the obturator and trocar of FIG. 11 partially advanced through the tissue.
Figure 13:
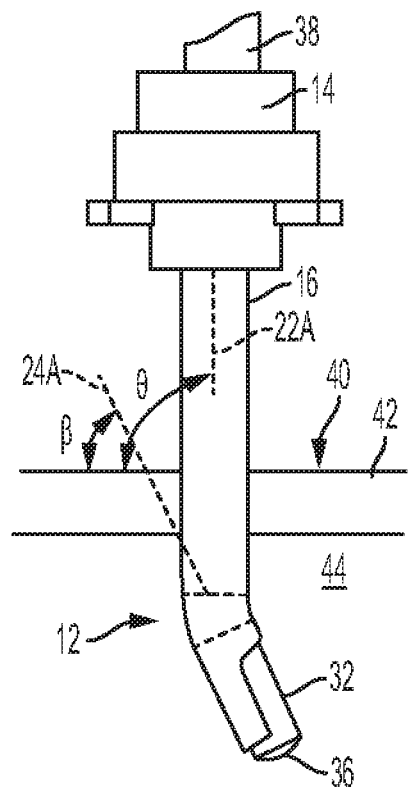
FIG. 13 is a side view of the obturator and trocar of FIG. 12 advanced further through the tissue.

The obturator's intermediate portion 32i is configured to move between a first state, in which the intermediate portion 32i is not flexed, and a second state, in which the intermediate portion 32i is flexed in a lateral or side-to-side direction. The first state is the default state of the intermediate portion 32i. In the first state, which is shown in FIGS. 7-10, a longitudinal axis 38i of the intermediate portion 32i is coaxially aligned with a longitudinal axis 38p of the proximal portion 32p and a longitudinal axis 38t of the distal tip portion 32t. In the second state, which is shown in FIGS. 11-13 discussed further below, the longitudinal axis 38i of the intermediate portion is coaxially aligned with the longitudinal axis 38t of the distal tip portion 32t and is transverse to the longitudinal axis 38p of the proximal portion 32p such that a distal portion of the obturator 28 including the intermediate portion 32i and the distal tip portion 32t extends at an angle with respect to the proximal portion 32p. The angle of the intermediate portion 32i and the distal tip portion 32t with respect to the proximal portion 32p is defined by an angle of the curved portion of the trocar in which the obturator is disposed. The angle of the trocar and the angle of the obturator may therefore be substantially equal. A person skilled in the art will appreciate that a value may not be precisely at a particular value but nevertheless be considered to be substantially at that value for any of a variety of reasons, such as manufacturing tolerances and sensitivity of measurement equipment. The intermediate portion 32$i$ being flexible at a variety of angles facilitates use of the obturator 28 with different trocars each having a curved portion at a different angle.

The intermediate portion 32$i$ is configured to automatically move between the first and second states in response to sliding within a trocar having a curved portion. When the intermediate portion 32$i$ is sliding distally within the trocar, the intermediate portion 32$i$ is configured to move from the first state to the second state, e.g., the intermediate portion 32$i$ is configured to flex in response to moving into and distally along the curved portion. When the intermediate portion 32$i$ is sliding proximally within the trocar, the intermediate portion 32$i$ is configured to move from the second state to the first state, e.g., the intermediate portion 32$i$ is configured to flex in response to moving out of and proximally along the curved portion.

The elongate shaft 32 and the proximal, intermediate, and distal portions 32$p$, 32$i$, 32$t$ thereof can have a variety of longitudinal lengths. An overall longitudinal length of the elongate shaft 32 (e.g., the sum of the longitudinal lengths of the proximal, intermediate, and distal portions 32$p$, 32$i$, 32$t$) is configured to be longer than a longitudinal length of a tubular elongate body of a trocar in which the elongate shaft 32 is slidably disposed to allow the obturator's distal tip 36 to be located distally beyond a distal end of the trocar while the handle 30 is located proximal to the trocar. With the elongate shaft 32 disposed within the trocar's inner lumen and the obturator's distal tip 36 located distally beyond a distal end of the trocar, the distal tip 36 is configured to lead the trocar and obturator 28 as a unit through tissue to facilitate positioning of the trocar within the tissue.

The obturator 28 can be made from any of a variety of one more materials. In an exemplary embodiment, the material(s) are surgically safe. Examples of materials that can be used for rigid portions of the obturator 28, such as the proximal and distal tip portions 32$p$, 32$t$, include stainless steel and biocompatible plastics. Examples of materials that can be used for flexible portions of the obturator 28, such as the intermediate portion 32$i$, include rubber.

A trocar as described herein can be provided as part of a kit that also includes an obturator as described herein. Providing the trocar and the obturator as part of a kit may help ensure that the trocar is used with an obturator that is properly sized for insertion into the trocar and for extension an appropriate length distally beyond the trocar when positioned within the trocar. The kit can have the obturator pre-inserted into the trocar such that the trocar and obturator are ready for insertion into a patient as a unit. Alternatively, the trocar without the obturator inserted therein can be provided in the kit, which may facilitate speedy use of the trocar without the obturator (e.g., insertion of the trocar into a body of a patient without the obturator disposed therein) and/or may facilitate user choice of different obturators to use with the trocar. The kit can include one or more trocars and one or more obturators, which may facilitate user choice of an appropriately sized trocar for insertion into a particular patient. In at least some embodiments, the kit can include one or more other elements in addition to one or more trocars and one or more obturators. For example, the kit can include at least one chest tube configured to be inserted into the trocar(s) included in the kit, which may help ensure that a chest tube that is properly sized for insertion into the trocar is used with the trocar and that the chest tube is readily available for use after trocar insertion into a patient.

As mentioned above, the trocars and obturators described herein can be used in a variety of surgical procedures. In general, the surgical procedure can be a procedure in which access into a body cavity is desired. For example, as mentioned above, the surgical procedure can be a thoracic surgical procedure in which access into a thoracic cavity is desired to, e.g., insert a chest tube therein. FIGS. 11-13 illustrate one embodiment of a method of use of a trocar in a surgical procedure. The method of FIGS. 11-13 is shown using the trocar 10 of FIGS. 1-6 and the obturator 28 of FIGS. 7-10, but the method can be similarly performed using other embodiments of trocars and obturators described herein. Additionally, although the method of FIGS. 11-13 is shown with the trocar 10 being inserted into a patient with an obturator disposed therein, the trocar 10 can instead be inserted into a patient without an obturator disposed therein.

As shown in FIG. 11, the trocar 10 with the obturator 28 disposed therein is positioned near an exterior surface 40 of tissue 42, e.g., an exterior skin surface, in which the trocar 10 is to be positioned. Then, as shown in FIG. 12, the trocar 10 and obturator 28 are advanced as a unit distally into the tissue 42, with the obturator's distal tip 36 leading the trocar 10 and obturator 28 through the tissue 42, until the trocar 10 and obturator 28 enter a body cavity 44 underlying the tissue 42. The trocar 10 is initially advanced into the tissue 42 with the longitudinal axis 24A of the trocar's distal portion 24 substantially perpendicular to the tissue surface 40, e.g., at a substantially 90° angle β, and with the longitudinal axis 22A of the trocar's proximal portion 22 at an obtuse angle θ relative to the tissue surface 40. A person skilled in the art will appreciate that the relative positions may not be precisely perpendicular but nevertheless be considered to be substantially perpendicular for any of a variety of reasons, such as manufacturing tolerances and sensitivity of measurement equipment. The trocar 10 and the obturator 28 continue to be advanced as a unit through the tissue 42, as shown in FIG. 13, until the trocar's curved portion 12 enters the body cavity 44. The curved portion 12 steers the trocar 10 and the obturator 28 to be at an adjusted angular position relative to the tissue 42, with the angle β between the longitudinal axis 24A of the trocar's distal portion 24 and the tissue surface 40 now being an acute angle that is less than 90° and with the angle θ between the longitudinal axis 22A of the trocar's proximal portion 22 and the tissue surface 40 now being substantially 90°. The trocar 10 and obturator 28 can continue being advanced distally as a unit through the tissue 42 until the housing's distal surface 20 abuts the tissue surface 40, or the obturator 28 can be removed from the trocar 28 (e.g., by being pulled proximally within the inner lumen 18) before the abutment of the surfaces 20, 40. Regardless of when or if abutment of the surfaces 20, 40 occurs, the obturator 28 is removed from the trocar 10. With the obturator 28 removed from the trocar 10, a surgical tool (e.g., a chest tube, etc.) can be advanced from outside the patient and through the inner lumen 18 of trocar 10 to pass through the tissue 42 and access the body cavity 44. The curved portion 12 of the trocar 10 positioned within the body cavity 44 allows the surgical tool to enter and be positioned within the body cavity 44 at an angle for better, more predictable positioning of the surgical tool within the body cavity 44 than if the trocar 10 was not curved.

A person skilled in the art will appreciate that the embodiments described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, consisting essentially of:
a trocar configured to be positioned in tissue of a patient to allow access therethrough into a body cavity of the patient, the trocar including a tubular elongate body having a proximal portion defining a first longitudinal axis, wherein the tubular elongate body is rigid, the tubular elongate body having a distal portion defining a second longitudinal axis that is transverse to the first longitudinal axis such that the distal portion extends linearly at a fixed angle not subject to or able to be changed with respect to the proximal portion, the tubular elongate body having an inner lumen extending through the proximal and distal portions, the inner lumen being configured to slidably receive a surgical tool therein to allow passage of the surgical tool therethrough from outside the patient to inside the body cavity, and the tubular elongate body having a cut-out in a sidewall thereof at a distal-most end of the tubular elongate body.

2. The device of claim 1, wherein a longitudinal length of the distal portion is less than a longitudinal length of the proximal portion.

3. The device of claim 1, wherein the angle is in a range of about 120° to 170°.

4. The device of claim 1, wherein the trocar has a proximal housing from which the tubular elongate body distally extends, a distal surface of the proximal housing being configured to abut an exterior surface of the tissue through which the tubular elongate body extends.

5. The device of claim 1, wherein the cut-out extends proximally from the distal-most end of the tubular elongate body and has a longitudinal length that is less than a total longitudinal length of the distal portion.

6. The device of claim 1, wherein the cut-out interrupts a circumference of the distal portion of the tubular elongate body such that a first portion of the distal portion of the tubular elongate body has an O-shaped cross-sectional shape and a remainder of the distal portion of the tubular elongate body, which is distal to the first portion, has a C-shaped cross-sectional shape.

7. A surgical system, consisting essentially of:
a trocar configured to be positioned in tissue of a patient to allow access therethrough into a body cavity of the patient, the trocar including a tubular elongate body having a proximal portion defining a first longitudinal axis, wherein the tubular elongate body is rigid, the tubular elongate body having a distal portion defining a second longitudinal axis that is transverse to the first longitudinal axis such that the distal portion extends linearly at a fixed angle not subject to or able to be changed with respect to the proximal portion, the tubular elongate body having an inner lumen extending through the proximal and distal portions, and the tubular elongate body having a cut-out in a sidewall thereof at a distal-most end of the tubular elongate body; and
an obturator configured to be inserted into the inner lumen and advanced distally therethrough such that a rigid distal tip of the obturator is located distally beyond the tubular elongate body, the obturator having an elongate shaft with a rigid proximal portion and a flexible intermediate portion located between the rigid proximal portion and the rigid distal tip, the flexible intermediate portion being configured to bend within the distal portion of the tubular elongate body.

8. The system of claim 7, wherein the flexible intermediate portion has a first state, in which a longitudinal axis thereof is coaxially aligned with a longitudinal axis of the rigid proximal portion and a longitudinal axis of the rigid distal tip, and a second state, in which the longitudinal axis of the flexible intermediate portion is coaxially aligned with the longitudinal axis of the rigid distal tip and is transverse to the longitudinal axis of the rigid proximal portion such that a distal portion of the obturator including the flexible intermediate portion and the rigid distal tip extends at a second angle with respect to the rigid proximal portion.

9. The system of claim 7, wherein the obturator has a blunt end configured to penetrate through the tissue of the patient to lead the trocar and the obturator into the body cavity.

10. The system of claim 7, wherein the obturator is configured to be removed from the inner lumen by being slid proximally therethrough.

11. The system of claim 7, wherein the cut-out extends proximally from the distal-most end of the tubular elongate body and has a longitudinal length that is less than a total longitudinal length of the distal portion.

12. The system of claim 7, wherein the cut-out interrupts a circumference of the distal portion of the tubular elongate body such that a first portion of the distal portion of the tubular elongate body has an O-shaped cross-sectional shape and a remainder of the distal portion of the tubular elongate body, which is distal to the first portion, has a C-shaped cross-sectional shape.

13. A surgical method, consisting essentially of:
advancing a trocar and an obturator as a unit through tissue of a patient at an angle relative to a surface of the tissue until distal ends of each of the trocar and obturator enter a body cavity underlying the tissue, and then changing the angle of the trocar and the obturator relative to the surface of the tissue, wherein the trocar includes a tubular elongate body having a proximal portion defining a first longitudinal axis, the tubular elongate body having a distal portion defining a second longitudinal axis that is transverse to the first longitudinal axis such that the distal portion extends linearly at a fixed angle not subject to or able to be changed with respect to the proximal portion, wherein the tubular elongate body is rigid;
after changing the angle relative to the surface of the tissue, removing the obturator from the trocar; and
after removing the obturator from the trocar, and with the longitudinal axis of the proximal portion of the trocar being substantially perpendicular to the surface of the tissue, advancing a chest tube through the elongate tubular body of the trocar and into the body cavity from outside the patient; wherein:
the obturator is located within an inner lumen of the trocar with a distal tip of the obturator located distal to the trocar and leading the unit through the tissue, wherein the distal tip of the obturator is rigid,
the angle at which the trocar and the obturator are advanced through the tissue is defined by the distal portion of the trocar extending linearly at the fixed angle not subject to or able to be changed relative to the proximal portion of the trocar, and the angle is changed such that the longitudinal axis of the proximal portion of the trocar is substantially perpendicular to the surface of the tissue.

14. The method of claim 13, wherein the trocar has a cut-out in a sidewall thereof at a distal-most end of the trocar, and the cut-out faces upward during the advancement of the trocar and obturator through the tissue.

15. The method of claim 14, wherein the cut-out interrupts a circumference of the distal portion of the tubular elongate body such that a first portion of the distal portion of the tubular elongate body has an O-shaped cross-sectional shape and a remainder of the distal portion of the tubular elongate body, which is distal to the first portion, has a C-shaped cross-sectional shape.

16. The method of claim 14, wherein the cut-out is on a side of the elongate tubular body aligned with the second longitudinal axis of the distal portion.

17. The method of claim 13, wherein the fixed angle is in a range of about 120° to 170°.

18. The method of claim 13, wherein the body cavity is a thoracic cavity.

19. The method of claim 13, further comprising, before advancing the trocar and the obturator as the unit through the tissue of the patient, inserting the obturator into the trocar and advancing the obturator distally within the trocar until the distal tip is located distal to the trocar.

20. The method of claim 19, wherein the obturator has an elongate shaft with a rigid proximal portion and a flexible intermediate portion located between the rigid proximal portion and the rigid distal tip, and the flexible intermediate portion automatically bends within the distal portion of the tubular elongate body during the distal advancement of the obturator within the trocar.

* * * * *